United States Patent [19]

Muller

[11] Patent Number: 5,061,269

[45] Date of Patent: Oct. 29, 1991

[54] SURGICAL RONGEUR POWER GRIP STRUCTURE AND METHOD

[75] Inventor: George H. Muller, Ann Arbor, Mich.

[73] Assignee: Joseph J. Berke, Detroit, Mich.

[21] Appl. No.: 571,031

[22] Filed: Aug. 21, 1990

Related U.S. Application Data

[63] Continuation of Ser. No. 306,857, Feb. 7, 1989, abandoned.

[51] Int. Cl.$^5$ ............................................. A61B 17/56
[52] U.S. Cl. ......................................... 606/83; 606/53; 606/167; 606/151; 81/57.44; 81/300
[58] Field of Search ..................... 604/22; 294/100; 606/83, 84, 79, 184, 167, 151, 53; 123/252, 142.5 R; 60/513, 512, 508; 81/300, 57.44

[56] References Cited

U.S. PATENT DOCUMENTS

| | | | |
|---|---|---|---|
| 3,477,226 | 11/1969 | Percival | 60/517 |
| 3,752,161 | 8/1973 | Bent | 128/303 X |
| 3,776,238 | 12/1973 | Peyman et al. | 128/305 |
| 3,842,839 | 10/1974 | Malis et al. | 128/318 X |
| 4,385,494 | 5/1983 | Golben | 60/513 X |
| 4,416,113 | 11/1983 | Portillo | 60/513 |
| 4,601,170 | 7/1986 | Fiege | 60/513 |

FOREIGN PATENT DOCUMENTS

2547185  4/1977  Fed. Rep. of Germany ... 128/303 R

*Primary Examiner*—Michael H. Thaler
*Attorney, Agent, or Firm*—Dykema Gossett

[57] ABSTRACT

Power assisted gripping structure and method comprising a surgeon's rongeur including two elongated relatively axially moveable members having at one end thereof structure for gripping, cutting or crushing material, handle means for manually moving the elongated members axially relative to each other, electrically actuated power assist cylinder structure connected between the elongated members for assisting in producing relative movement between the elongated members on actuation thereof and switch structure for actuating the power cylinders in multiple stages. In different modifications, the structure for gripping, cutting or crushing material may be a Kerrison or Leksell rongeur tip. Alternatively, the structure for gripping, cutting or crushing may be adjustable wrench, spreader, prier suction cup or lifter structure and the power assisted gripping structure may be used in industry such as in robotics as well as in medical applications. The method of the invention comprises the steps of power assisting actuation of a surgeon's rongeur or the like with electrically actuated power cylinders and actuating the cylinders in pulsed steps and in multiple stages.

30 Claims, 5 Drawing Sheets

SURGICAL RONGEUR POWER GRIP STRUCTURE AND METHOD

This is a continuation of U.S. Pat. Ser. No. 07/306,857 filed on Feb. 7, 1989, now abandoned.

BACKGROUND OF THE INVENTION

1. Field of the Invention

The invention relates to power grip structures and methods and refers more specifically to an electrically actuated power assisted surgeon's rongeur which may be actuated in multiple stages and the method of using the power assisted surgeon's rongeur including electrically actuating power assist structures, some in multiple stages.

2. Description of the Prior Art

In the past, surgeon's rongeurs of both the Kerrison and Leksell types have generally been manually actuated structures wherein squeezing of relatively pivoted handles constructed much like plier handles has produced a punching or scissor-like cutting action due to relative movement of two parallel elongated members secured to the handles and having gripping or crushing means at one end thereof. Such structure is tiring when gripped repeatedly to open a human skull for example. Further such structure unnecessarily increases the time to perform such procedure and thus prolongs operating time which is undesirable for both patient and surgeon.

A few power operated rongeurs have been suggested in the past. They have, however, been hydraulically or pneumaticaly actuated and thus have required access to gas or hydraulic fluid under pressure by means of heavy and cumbersome pressure lines and thus are undesirable. Further, such power assisted surgeon's rongeurs as have been available in the past have been particularly complicated and lacked feedback in the handle to provide the operator with a direct appreciation of the resistance to cutting and therefore the need for more or less assist power, and also were expensive to manufacture and inefficient in use.

SUMMARY OF THE INVENTION

The rongeur structure and method of the invention is electrically actuated through thin and light wires to provide a power assisted grip which may be actuated in multiple stages, without the encumbrances and weight drag of heavy and large hydraulic or pneumatic connecting lines.

The rongeur structure of the invention comprises two side by side elongated members having gripping, cutting or crushing means at one end thereof operable on relative axial movement between the elongated members to grip, cut or crush desired material. A first handle part is integrally constructed with the other end of one of the elongated members, a second handle part is pivotally secured to the first handle part adjacent the other end of the first elongated member and engages the other end of the other elongated member in a lost motion connection.

In one preferred embodiment of the invention, a pair of electically actuated power cylinders are secured between the one handle part and the other end of the other elongated member whereby on energizing the electrically actuated power cylinders relative longitudinal movement is produced between the elongated members.

In another embodiment of the invention, three electrically actuated power cylinders are secured between the one handle part and the other end of the other elongated member and means are provided for manually closing a switch to energize the electrically actuated power cylinders in multiple stages, using the cylinders independently or in groups.

A plurality of gripping, cutting and crushing means such as wrench, spreader, prier, lifter, and suction cup means as well as various rongeur-type tips such as Kerrison and Leksell rongeur tips may be utilized with the power grip structures of the invention.

Further, the invention is not limited to rongeurs but may also be useful in constructing electrical power actuated adjustable self-tightening wrenches, spreaders, priers, lifters, shears, pliers, snips, nibblers, suction grippers and the like, useful in industries such as in robotics, for example.

In accordance with the method of the invention, power cylinder structure is electrically actuated to assist in rongeur or other tool operation. The method of the invention includes multiple stage actuation of electrically actuated power cylinders in groups where a plurality of power cylinders are provided.

BRIEF DESCRIPTION OF THE DRAWINGS

FIG. 13 is a side view of suction cup gripping means which may be substituted for the rongeur tips of FIGS.

1, 7 and 10, the adjustable wrench-type gripping means of FIG. 11 and the spreader structure of FIG. 12.

DESCRIPTION OF THE PREFERRED EMBODIMENT

Figures 1, 2, 3:
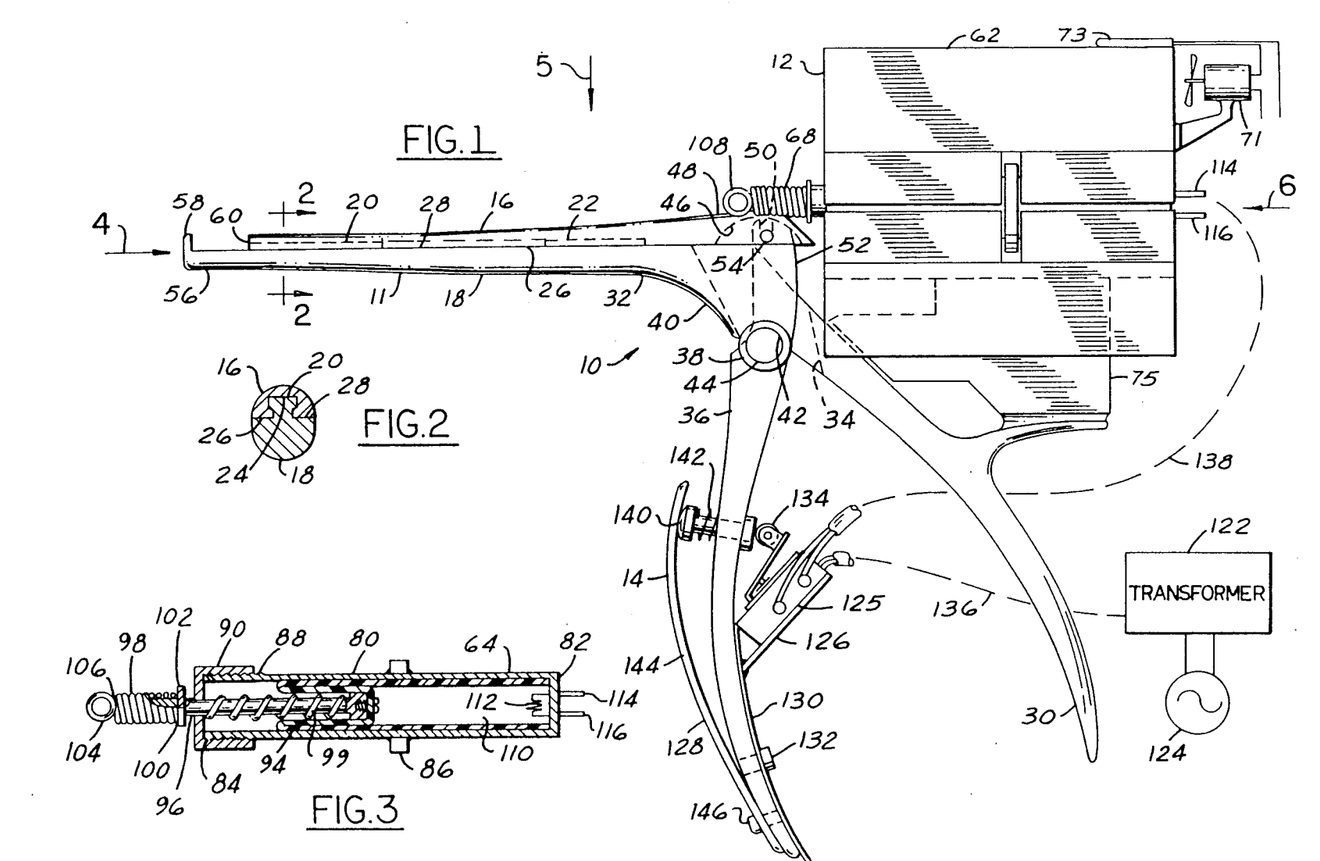
FIG. 1 is a side view of a surgical rongeur constructed in accordance with the invention for effecting the method of the invention.
FIG. 2 is an enlarged section view of the rongeur structure illustrated in FIG. 1 taken substantially on line 2—2 in FIG. 1.
FIG. 3 is a longitudinal section view of one of the electrically actuated power cylinders of the rongeur structure of FIG. 1.

As shown best in FIG. 1 the power grip structure of the invention is a surgeon's rongeur 10. The power assisted surgeon's rongeur 10 as shown in FIG. 1 includes manual rongeur structure 11, electrically actuated power assist structure 12 and manual actuating means 14 for the power assist structure.

More specifically, the power assisted rongeur structure 10 includes a pair of elongated parallel, generally straight members 16 and 18 which are in side by side, sliding arrangement as shown in FIG. 1. As shown in FIG. 2 the elongated member 18 is a slide and has guides 20 and 22 spaced apart longitudinally thereof which are generally T-shaped in cross section to ensure positive interdigitation. The elongated member 16 has a T-shaped recess 24 in the surface 26 thereof for receiving the guides 20 and 22 of the elongated member 18 whereby the surface 26 of the elongated member 16 and the surface 28 of the elongated member 18 are held in surface to surface sliding engagement.

Figures 4, 5, 6:
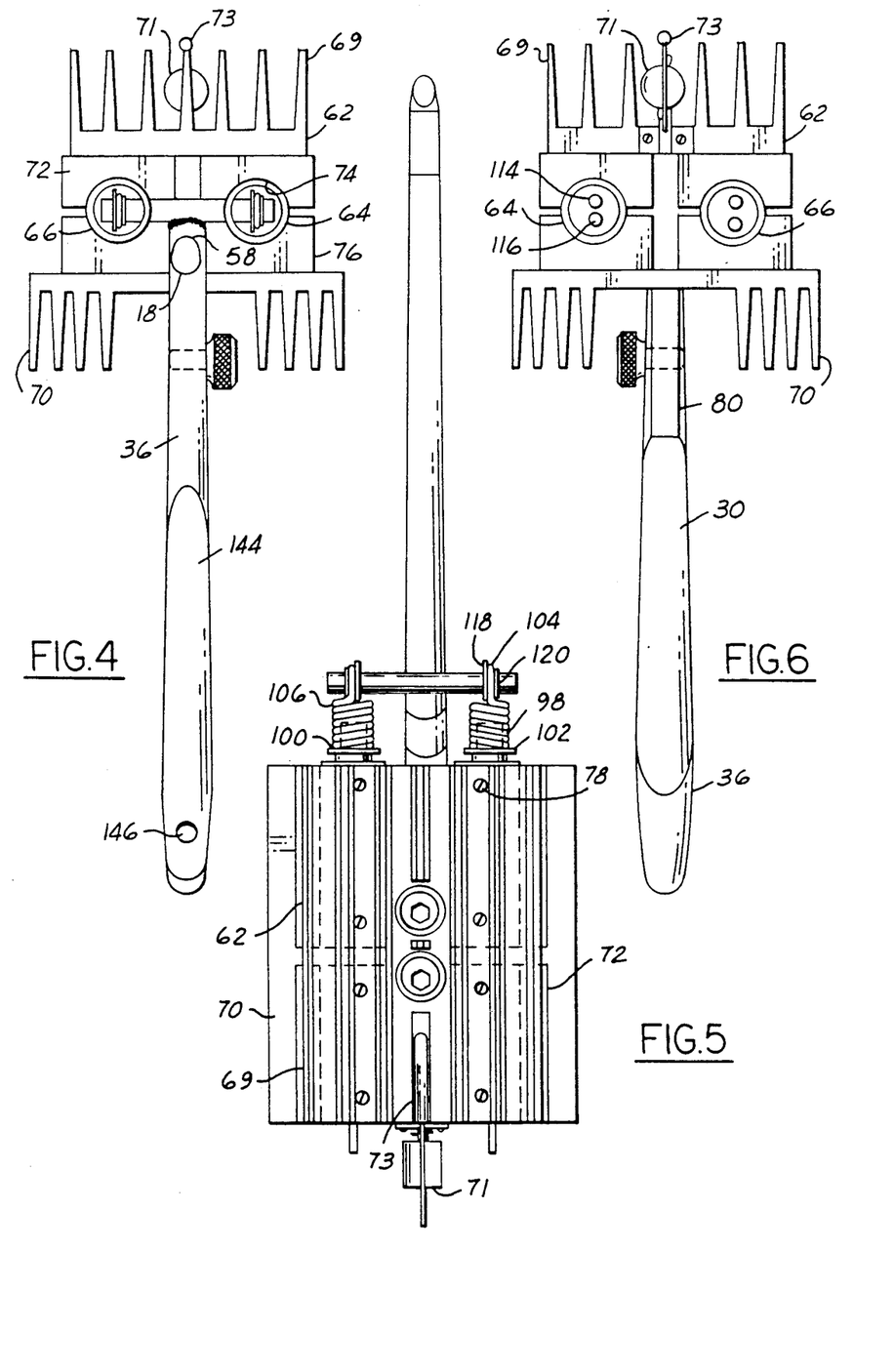
FIG. 4 is an end view of the rongeur structure illustrated in FIG. 1 taken in the direction of arrow 4 in FIG. 1.
FIG. 5 is a top view of the rongeur structure illustrated in FIG. 1 taken substantially in the direction of arrow 5 in FIG. 1.
FIG. 6 is another end view of the rongeur structure illustrated in FIG. 1 taken substantially in the direction of arrow 6 in FIG. 1.

A handle part 30 shaped as shown in FIGS. 1 and 6 is constructed integrally with the elongated slide member 18 at the end 32 thereof. As shown, the handle part 30 has an opening 34 extending therethrough, through which a second handle part 36, which will be considered subsequently, extends. Handle part 30 is also provided with transversely spaced apart projections 38 at end 40 thereof having openings 42 therethrough for receiving a pivot pin 44 which pivotally mounts handle part 36 in the opening 34.

The elongated member 16 is provided with a recess 46 in end 48 thereof having an arcuate longitudinally extending cross section as shown thus in FIG. 1. Handle part 36 as shown best in FIGS. 1 and 4 includes a slot 50 in the end 52 thereof for receiving a pin 54 secured in the elongated member 16 at end 48 thereof and extending across recess 46 to ensure a lost motion connection between handle part 36 and elongated member 16.

The end 56 of the elongated member 18 is terminated in a portion 58 which extends at right angles to the end 56 as shown best in FIG. 1. The terminal portion 58 of the elongated member 18 of the rongeur structure 10 shown in FIG. 1 cooperates with the end 60 of the elongated member 16 to grip, cut or crush material placed between the terminal portion 58 of the elongated member 18 and the end 60 of the elongated member 16 on movement of the end 60 of the elongated member 16 towards the portion 58 of the end 56 of the elongated member 18.

The manual rongeur structure 11 so far described is a Kerrison-type surgeon's rongeur The terminal portion 58 of the elongated member 18 and the end 60 of the elongated member 16 may in the usual fashion of surgeon's rongeurs be formed to effect the gripping, cutting and/or crushing operation as desired.

In accordance with the invention, the power assist structure 12 is provided to assist a surgeon in actuating the manual rongeur structure 11. The power assist structure 12 makes the surgeon's task in operating the power assisted rongeur structure 10 less difficult in that it requires much less manual gripping pressure by the surgeon when it is used. Further, due to the increased number of actuating cutting cycles per unit of time that improved rongeur 10 may now provide because of the power assist structure 12, overall surgical time is reduced which is beneficial both to the patient and the surgeon.

The power assist structure 12 includes, heat sink structure 62 shown best in FIGS. 1 and 4 through 6 secured to the handle part 30, power assist cylinders 64 and 66 mounted in the heat sink structure 62 and means 68 for securing the power cylinders 64 and 66 to the end 48 of the elongated member 16 of the power assisted rongeur 10.

The type of electrically actuated power cylinder used in the invention is functionally based on the use of a gas expanding when heated within the cylinder by a resistor heated under the application of an electrical current. To stop the gas expanding the current is cut off and the excess heat is dissipated in the cylinder surrounding heat sink structure.

More specifically the heat sink structure 62 includes an upper and lower heat sink member 69 and 70 respectively, four generally rectangular heat sink portions 72 which are similar and which include a part cylindrical recess 74 in one face thereof are secured to the upper and lower heat sink members 69 and 70 by convenient means such as screws 78 as illustrated best in FIG. 5.

If desired, and as shown diagramatically in FIG. 1 a small fan 71 may be secured to the heat sink structure 62 to aid in dissipation of heat. When the fan 71 is provided, concurrently with the cylinder being switched off or when so dictated by thermal feedback (i.e. through a thermocouple switch conventional structure 73 secured to one of the fins) the fan 71 is switched on to accelerate heat dissipation from the fins of the heat sink structure.

As shown best in FIGS. 1 and 4 through 6 the assembled heat sink members are arranged to secure the electrically actuated power cylinders 64 and 66 therebetween and are secured to the handle part 30 by means of bolts extending through the top heat sink member 69, between the heat sink members 72 and through the bottom heat sink member 70 into a vertically extending support member 75 welded or otherwise secured to the handle part 30, The electrically actuated power cylinders 64 and 66 which are identical are shown best in FIG. 3 wherein the electrically actuated power cylinder 64 is shown in longitudinal section. Cylinder 64 includes an outer hollow cylindrical case 80 having a closed end 82 and an open end 84. A cylindrical flange 86 adapted to fit between the heat exchange members 72 in assembly with the heat exchange structure 62 is provided substantially centrally of the cylindrical case 80. The end 84 of the case 80 has a threaded portion 88.

A cap 90 is provided extending over the end 84 of the case 80 to threadedly engage the thread 88 on the case 80. The end 92 of a flexible diaphragm 94 in a gas-tight seal in the end 82 of the case 80 is secured. Piston rod 96 extends through the cap 90 and is secured centrally to the diaphragm 94 as shown in FIG. 3. Spring 99 biases diaphragm 94 to the right, against the gas pressure in chamber 110. Diaphragm 94 thus forms a rolling sleeve as the piston rod 96 extends out of and retracts into case 80.

Spring 98 is secured at end 100 to rod 96 by convenient means such as disc or flange 102 and is provided with the loop 104 at the end 106 thereof by which the end 106 of the spring 98 may be secured to pin 108 welded or otherwise secured to the end 48 of the elongated member 16 of the rongeur 10 as shown best in FIG. 1.

The chamber 110 formed between the case 80 and the diaphragm 94 is filled with a gas such as Freon which expands rapidly when subjected to heat and which will contract rapidly when heat is removed therefrom. An electrical heating resistance 112 is placed within the end 82 of the casing 80 and is energized through the electrical conductors 114 and 116 by the actuating means 14 as will be seen subsequently.

The electrically actuated power cylinders 64 and 66 may be actuated by a 12 volt direct current electrical signal placed across the conductors 114 and 116 which signal is operable to heat the resistor 112 to expand the inert fluorocarbon gas in chamber 110. The electrically actuated power cylinder 64 has a cycle life of approximately 10,000 expansions at 3 seconds to 4 seconds per expansion and retracting cycle (expands in approximately 1/5 of a second and cools off in approximately 2 and 4/5 seconds). The cylinders 64 and 66 have an expanding force of approximately 40 lbs.

The means 68 for securing the cylinders 64 and 66 to the elongated member 16 previously indicated includes the spring 98 sleeved over the outer end of the rod 96 and having an inner end 100 secured to the disc or flange 102 which in turn is secured to the rod 96 and the pin 108 which, as shown best in FIGS. 1 and 5 is welded to the end 48 of the elongated member 16. The loops 104 on the ends 106 of the springs 98 are positioned over the ends of the pin 108 as shown best in FIG. 5 and are held between the retaining rings or discs 118 and 120 also sleeved over the ends of the pin 108.

The actuating means 14 for the power assist structure 12 includes the transformer 122 for transforming 115 volt 60 cycle electrical energy from the source of alternating electrical energy 124 to a 12 volt direct current signal, switch structure 126 and structure 128 for operating the switch structure 126.

More specifically, the switch structure 126 includes bracket 130 which is adjustably secured to the handle part 36 by the screw 132 and limit switch 125. The limit switch 125 includes the pivoted arm 134 which when pivoted clockwise toward the limit switch 125 as shown in FIG. 1, closes the limit switch 125 to complete an electrical circuit from the transformer 122 through the limit switch 125 to the electrically actuated power cylinders 64 and 66 through conductors 136 and 138.

The lever 134 of the limit switch 125 is caused to pivot clockwise by the spring biased plunger 140 of the actuating structure 128 on movement of the plunger 140 to the right in FIG. 1. Besides the plunger 140 the actuating structure 128 includes the biasing spring 142 and the leaf spring 144 secured to the handle part 36 of the rongeur 10 by convenient means such as the screw 146.

In overall operating of the power assisted rongeur 10 as shown in FIGS. 1 through 6 when it is desired to actuate the rongeur 10 to grip, cut or crush material positioned between the end 60 of the elongated member 16 and the terminal portion 58 of the elongated member 18, the surgeon grips the handle parts 30 and 36 and squeezes them together in the manner of operation of manual rongeur 11. When sufficient pressure, for example, approximately 40 lbs. is applied between the handle parts 30 and 36 manually by the surgeon to place approximately 40 lbs. of pressure on the leaf spring 128, in combination with the spring 142, the plunger 140 is moved to the right in FIG. 1 to close the limit switch 125. The resistors 112 are heated in the power cylinders 64 and 66 to cause the gas therein to expand and move the rods 96 to the left in FIG. 1 with an ultimate force of approximately 40 lbs. each.

Initially, on actuation of the cylinders 64 and 66 the pressure on the surgeon's hand, due to squeezing the handle parts 30 and 36, is relieved since the spring 98 is allowed to collapse from its expanded position caused by initial manual actuation of the rongeur 10. When the spring 98 reaches its totally collapsed position, as shown in FIG. 1, the combined force of the electrically actuated power cylinders 64 and 66 is applied to the elongated member 16 through the pin 108 to assist the surgeon in gripping, cutting or crushing material placed between the end 60 of the elongated member 16 and the terminal portion 58 of the elongated member 18. The surgeon's task in cutting through bone and the like is thus greatly reduced to speed up surgery time and reduce surgeon fatigue.

After initial electrical actuation of the power cylinders 64 and 66, if the pressure is released by the surgeon, that, if his grip pressure falls below, for example, 40 lbs., the plunger 140 will again move to the left as shown in FIG. 1 to remove the electrical signal from the electrically actuated power cylinders 64 and 66 and the power cylinders 64 and 66 will cool and retract the rods 96. When the pressure exerted by the surgeon again exceeds the force of the leaf spring 128 in junction with the spring 142 the power cylinders 64 and 66 will again be actuated to provide the power assist to the manual rongeur 11. The rapid dissipation of the heat through the fins in turn rapidly cools the gas within the power cylinder to retract the rods. This allows the cylinder to return to an unactuated state and allows the rapid recycling of the power cylinder. Thus, the heat dissipating structure allows the cylinder to be cycled much more rapidly than it would in the absence of the heat sink structure.

Thus, in accordance with the invention, the power assisted rongeur 10 may be actuated in steps with the surgeon getting a number of time spaced power assists from the cylinders 64 and 66 as the gripping force of the surgeon varies about a selected value of, for example, 40 lbs. Ultimately, the maximum force which can be generated by the rongeur 10 is the force of the surgeon's grip plus the continuous force of the two electrically actuated power cylinders 64 and 66 which with each of the cylinders being a 40 lb. cylinder would amount to an additional 80 lbs.

Figure 7:
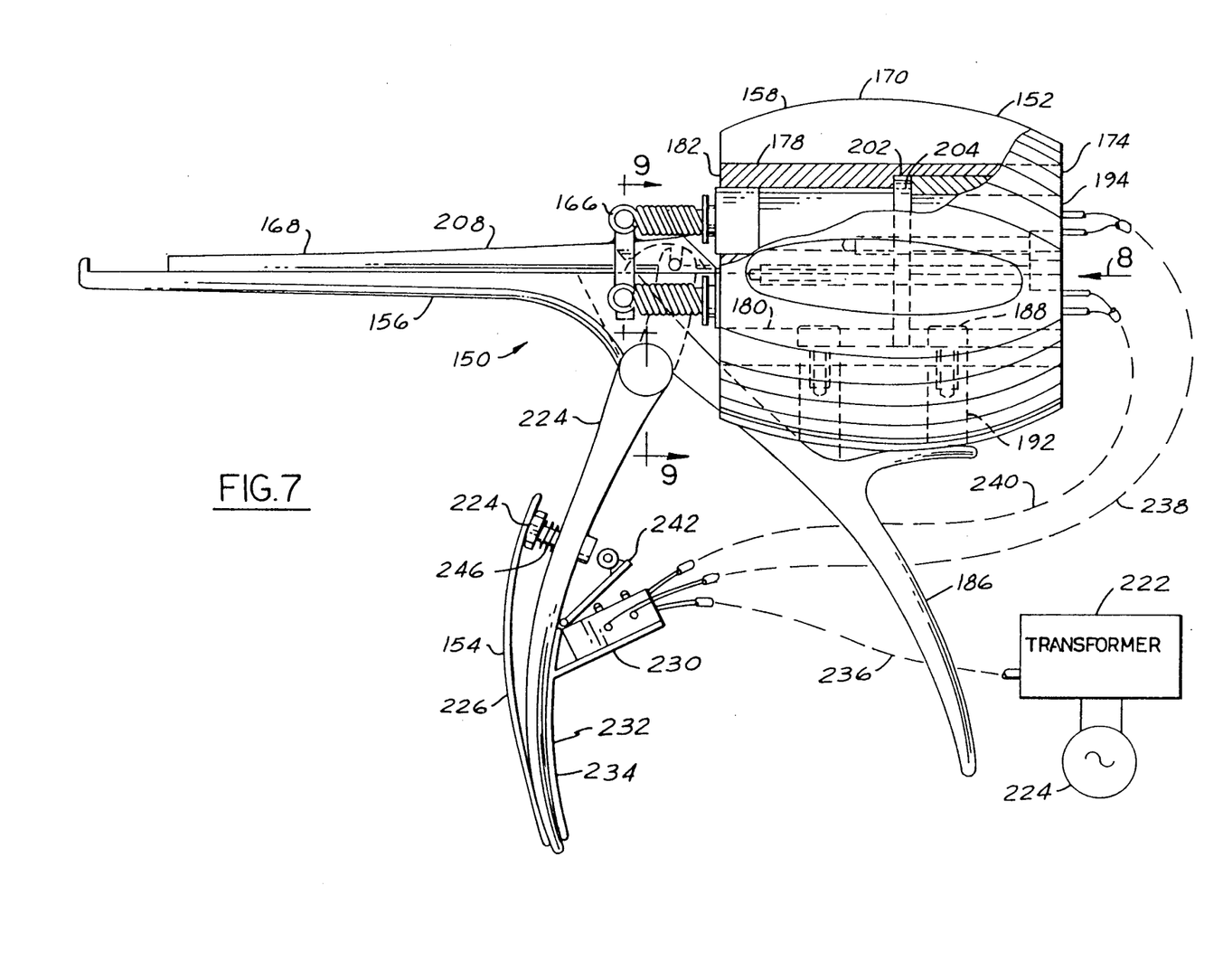
FIG. 7 is a side view of a second embodiment of the power assisted surgeon's rongeur of the invention for practicing the method of the invention.
Figure 8:
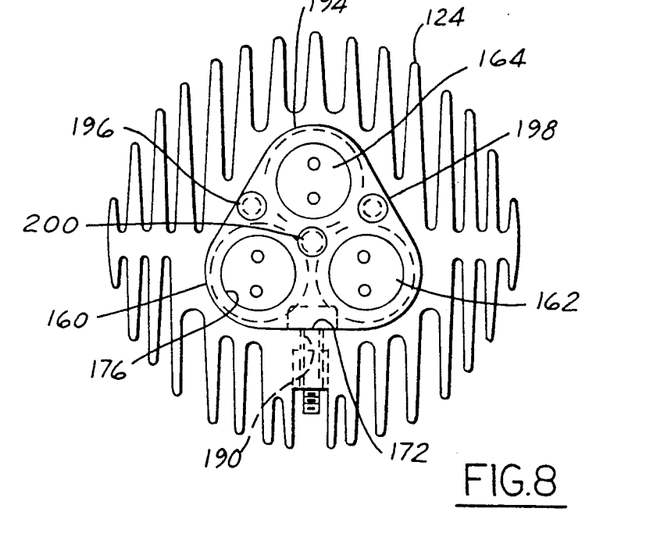
FIG. 8 is a partial rear view of the power grip, surgeon's rongeur structure illustrated in FIG. 7 taken in the direction of arrow 8 in FIG. 7.
Figure 9:
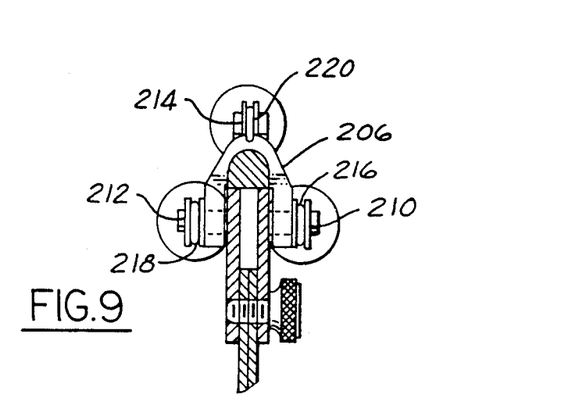
FIG. 9 is a partial section of the rongeur structure illustrated in FIG. 7 taken substantially on the line 9—9 in FIG. 7.

The embodiment 150 of the power grip rongeur of the invention shown in FIGS. 7 through 9 differs from the rongeur 10 shown in FIGS. 1 through 6 in the electrically actuated power assist structure 152 and in the actuating structure 154. The manual Kerrison-type rongeur structure 156 is the same as the manual rongeur structure 11 considered above.

The electrically actuated power assist structure 152 illustrated in FIGS. 7 through 9, as before, includes a heat sink structure 158, electrically actuated power cylinders 160, 162 and 164 and structure 166 for securing the power cylinders 160, 162 and 164 to the elongated member 168 of the manual rongeur structure 156.

As shown best in FIG. 7, the heat sink structure 158 includes a body member 170 having a substantially triangular recess 172 in end 174 thereof and three separate openings 176, 178 and 180 in the other end 182 thereof for receiving the power cylinders 160, 162 and 164 respectively. The heat dissipating fins 182 of the body member 170 may be of any desired spacing and shape to effect necessary heat dissipation from the heat sink structure 158 as required. The spacing and shape of the fins 182 as shown particularly in FIG. 8 are not therefore intended to be limiting.

The body member 170 of the heat sink structure 158 is then secured to the handle part 186 of the manual rongeur structure 156 by means of bolts 188 extending through transverse openings 190 in the heat sink body member 158 as shown best in FIG. 8 and into internally threaded hollow cylindrical studs 192 secured to the handle part 186 of rongeur structure 156 by convenient means such as welding.

The electrically actuated power cylinders 160, 162, and 164 which are the same type cylinders illustrated in FIG. 3 and disclosed above are inserted in the heat sink structure 158 as shown best in FIG. 8 and a generally triangular closure member 194 is placed in the recess 172 in the end 174 of the heat sink body member 158 and is secured to the heat sink body member 158 by means of the three screws 196, 198 and 200 best shown in FIG. 8. The triangular closure member 194 pinches the flanges of the power cylinders 161, 162 and 164 between the surface 202 of the body member 170 of the heat sink structure 158 and the end 204 of the triangular closure member 194.

The structure for securing the power actuating cylinders 160, 162 and 164 to the elongated member 168 of the rongeur structure 156 includes a yoke 206 welded or otherwise secured to the end 208 of the elongated member 168 having pins 210, 212 and 214 secured thereto for receiving the looped ends 216, 218 and 220 of the power cylinder springs in the manner considered above.

The actuating structure 154 as shown in FIG. 7, further includes the transformer 222 providing 12 volt direct current power from a 115 volt 60 cycle alternating current power supply 224 as before, leaf spring 226 and spring biased plunger 228.

However, limit switch 230 which is adjustably supported on bracket 232 secured to handle part 244 by means of screw 234 is a two level limit switch such that two separate circuits are completed between the transformer 222 and the electrically actuated power cylinders 160 and 162 as one group and the electrically actuated power cylinder 164 over conductors 236, 238 and 240 on progressive pivoting of the limit switch lever arm 242 in a clockwise direction as shown in FIG. 7.

Thus, on actuation of the embodiment of the power assisted surgeon's rongeur 150 shown in FIGS. 7 through 9, as the surgeon grips the handle parts 186 and 244 the first circuit through the limit switch 230, that is the circuit to energize the lower two power cylinders 160 and 162, is energized when the grip pressure of the surgeon reaches approximately 40 lbs. as felt through the leaf spring 154 and plunger spring 246. In the same manner as above the surgeon's grip may then be assisted by a full 80 lbs. pressure of the combined power cylinders 160 and 162. Again, the full 80 lbs. pressure can be applied in steps as considered above, on manipulation of the plunger 228 by released pressure of the surgeon's hand grip if desired.

If more pressure is desired, the surgeon's grip is tightened to slightly over 40 lbs. and the second circuit of the limit switch 230 is completed to energize the power cylinder 164 to provide an additional 40 lbs. pressure.

Thus, the maximum pressure that can be generated with the power assisted rongeur 150 is three times 140 lbs. pressure plus the grip of the surgeon. Again, as pointed out above, the pressure in both steps can be applied in pressure pulses on manipulation by the surgeon of his gripping of the rongeur and in particular his movement of the plunger 228.

While two embodiments of the power assisted surgeon's rongeur of the invention have been considered in detail above together with modifications thereof, it will be understood that other embodiments and modifications of the invention are contemplated.

Figure 10:
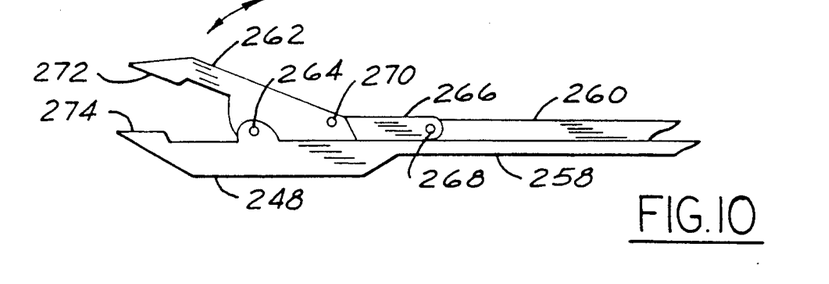
FIG. 10 is a side view of a Leksell-type rongeur tip which may be used with the power grip rongeur structures illustrated in FIGS. 1 and 7 in place of the Kerrison-type rongeur tip shown in FIGS. 1 and 7.

Thus, for example, as shown in FIGS. 10 through 15, the structure of the invention need not be a surgeon's rongeur and the tip on the surgeon's rongeur of the invention, need not be a Kerrison-type tip. The tip of either rongeur 10 or 150 may be, for example, a Leksell-type tip 248 as shown in FIG. 10 or another type of rongeur tip. Further, the structure of the invention as shown in FIGS. 11 through 15 may include operating tips which are an adjustable wrench 250, a spreader 252, a suction cup gripper 254, a prier 256, or a lifter 257, respectively for industrial as well as surgical use as desired.

As shown in FIG. 10, the Leksell-type rongeur tip 248 again includes the elongated members 258 and 260 which are movable longitudenly with respect to each other on T-shaped cross section guide members operable in a T-shaped slot as considered above. The end member 262 is mounted on the bottom elongated member 258 for pivoting about the pivot pin 264 and linkage 266 is pivotally connected to the elongated member 260 by the pivot means 268 and to the end member 262 by the pivot means 270. Thus, on movement of the elongated member 260 to the left in FIG. 10 with respect to the elongated member 258 the left end of linkage 266 as shown in FIG. 10 raises and the right end of the end member 262 raises and the linkage 266 and member 262 are pivoted with respect to each other above the pivot means 270 whereby material may be gripped, cut or crushed between the end 272 of the end member 262 and end 274 of the elongated member 258.

Figure 11:
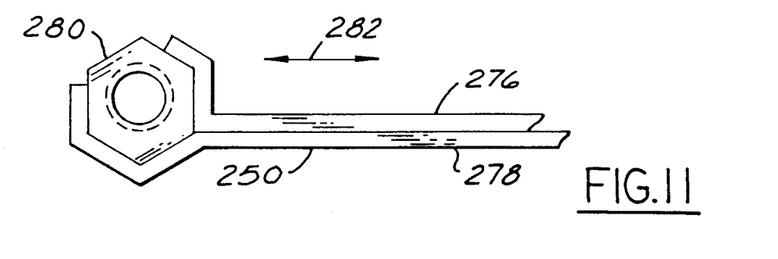
FIG. 11 is a side view of an adjustable wrench type gripping means which may be substituted for the rongeur tip structures of FIGS. 1, 7 and 10 in power grip structure similar to that shown in FIGS. 1 and 10.

As shown in the self-tightening, adjustable wrench of FIG. 11, the ends of the elongated members 276 and 278 are shaped to provide a partial hexagon internal surface whereby hexagonal nuts, bars or the like 280 may be gripped and released on reciprocal movement of the elongated member 276 in the direction of arrows 282 relative to the elongated member 278.

Figure 12:
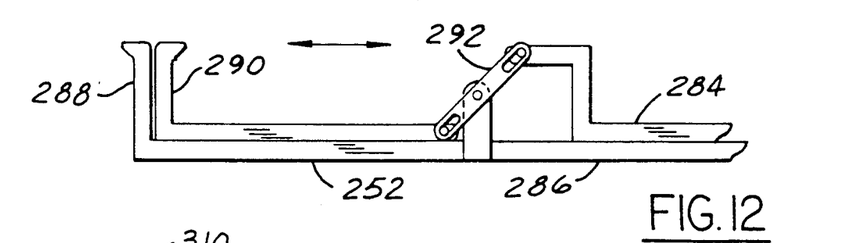
FIG. 12 is a side view of a spreader structure which may be substituted for the rongeur tips of FIGS. 1, 7 and 10 and the adjustable wrench-type gripping means of FIG. 11.

The spreader tip structure 252 illustrated in FIG. 12 again includes the two relatively movable elongated members 284 and 286. The end 288 of the member 286 is shaped as shown and a separate end member 290 also shaped as shown is provided on the elongated member 286. Both the members 284 and 290 are slideable on the elongated member 286 on T-shaped guide and recess structure as before. Lever type direction reversing structure 292 is provided between the elongated member 284 and the additional end member 290 as shown in FIG. 12 to provide movement of the members 284 and 290 toward each other on movement of the member 284 to the left with respect to member 286 in FIG. 12. A spreading action is thus provided between the ends 288 and 290 of the tip structure shown in the FIG. 12 which in accordance with the invention may be power assisted as above.

Figure 13:
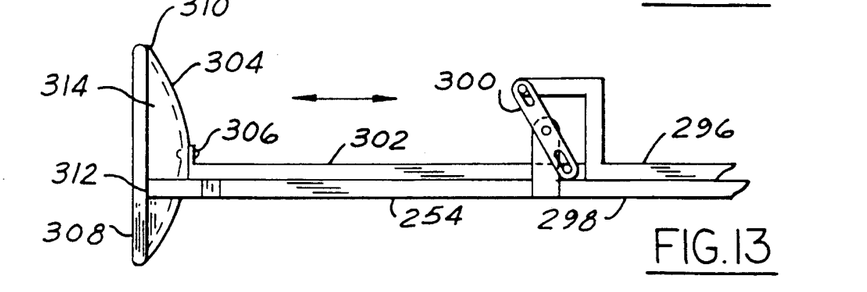

The vacuum gripping structure 254 illustrated in FIG. 13 again includes the parallel elongated members 296 and 298 and a motion reversing linkage structure 300 between the elongated member 296 and the additional member 302 both of which are adapted to slide along the elongated member 298 as above. The suction cup gripping structure illustrated in FIG. 13 further includes a flexible diaphragm 304 secured to the end 306 of the additional elongated member 302 as shown in FIG. 13. Annular sealing structure 308 is provided around the outer periphery 310 of the flexible diaphragm 304 which sealing structure is connected to the end 312 of the elongated member 298.

In use of the structure shown in FIG. 13 the member 302 is moved to the left as shown in FIG. 13 on movement of the member 296 to the right and the sealing structure 308 is urged into contact over a flat surface which it is desired to grip. The elongated member 296 is then moved to the left as shown in FIG. 13 whereby the center of the diaphragm 304 and the member 302 are moved to the right to create a suction in the sealed chamber 314 formed by an operator pressing the sealing structure 308 against the material he desires to grip. The drawing of the suction in the chamber 314 may thus be power assisted by electrically actuated power cylinders providing relative movement between the members 298 and 296 as above.

Figure 14:
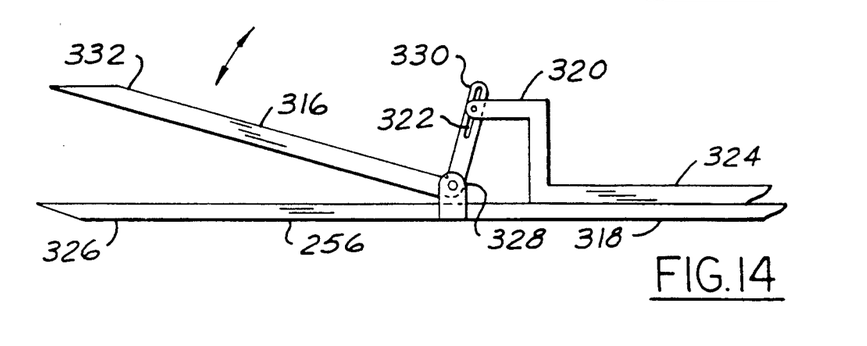
FIG. 14 is a side view of prior structure which may be substituted for any of the rongeur tips of FIGS. 1, 7 and 10, the adjustable wrench-type gripping means of FIG. 11, the spreader structure of FIG. 12 and the suction cup gripping means of FIG. 13 on power grip structure the same as or similar to that shown in FIGS. 1 and 10.

The prier structure 256 of FIG. 14 has a bell crank member 316 pivotally secured to the end of the elongated member 318 and again there is provided a lost motion connection due to the slot 322 in arm 330 of the bell crank lever 316 and the offset end 320 of the other elongated member 324. Relative movement of the elongated members 318 and 324 thus produces relative movement of the arm 332 of the bell crank 316 and the end 326 of the elongated member 318 about the pivot means 328 mounting the bell crank 316 on the elongated member 318.

Figure 15:
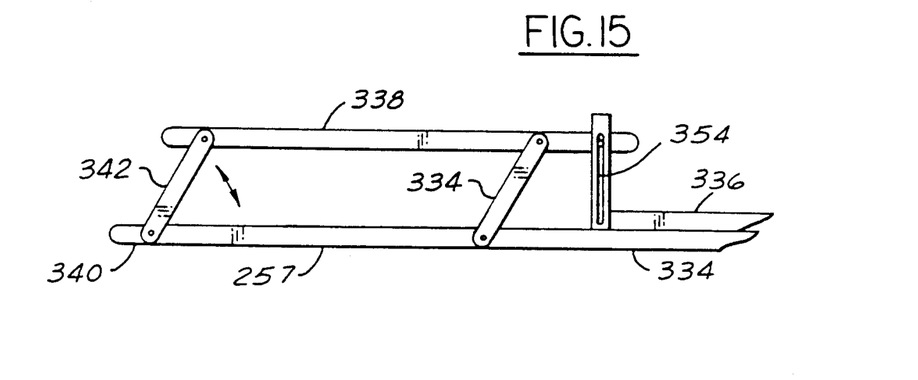
FIG. 15 is a side view of lifter structure which also may be substituted for any of the tips, gripping means and other structures shown in FIGS. 10 through 14 on power grip structure the same as or similar to that shown in FIGS. 1 and 10.

Lifter structure 257 as shown in FIG. 15 again includes the parallel, relatively slideable, elongated members 334 and 336, the relative longitudinal movement between which may be power assisted as above. A separate elongated member 338 is mounted on end 340 of elongated member 334 for parallel movement transverse of the member 334 or linkages 342 and 344 pivotally connected to the members 338 and 334 by pivot means 346 and 348 and 350 and 352 at their opposite ends as shown in FIG. 15 on reciprocal longitudinal movement of member 336 along member 334. Again, a lost motion pin and slot connection 354 is provided between the member 338 and the off-set end of member 336 to permit the parallel lifting movement between the members 338 and 334 on relative axial movement between the members 334 and 336.

I claim:

1. Power grip structure comprising two elongated members positioned in side by side parallel relation for relative longitudinal movement, means at one end of the members for gripping an object on relative axial movement between the members, said members being manually movable relative to each other for a predetermined distance, at least one electrically actuated power cylinder secured between the elongated members for producing relative axial movement between the members on actuation thereof and switch means connected to the power cylinder for communicating electric energy for actuation of the power cylinder after movement through said predetermined distance wherein the manual movement through said predetermined distance closes said switch means, which in turn actuates said power cylinder.

2. Structure as set forth in claim 1 wherein a plurality of electrically actuated power cylinders are connected between the elongated members and further including means for separately actuating the power cylinders in groups.

3. Structure as set forth in claim 1 wherein the power grip structure is a surgeons's rongeur having one of a Kerrison and Leksel type tip.

4. Structure as set forth in claim 1 wherein the means for gripping comprises self-tightening, adjustable wrench structure.

5. Structure as set forth in claim 1 wherein the means for gripping comprises separator structure.

6. Structure as set forth in claim 1 wherein the means for gripping comprises suction cup structure.

7. Structure as set forth in claim 1 wherein the means for gripping comprises prier structure.

8. Structure as set forth in claim 1 wherein the means for gripping comprises lifter structure.

9. A power grip structure as recited in claim 1, wherein manual input must be continued after the actuation of said electrically actuated power cylinder, or said electrically actuated power cylinder will become deactuated.

10. A power grip structure as recited in claim 1, wherein an electric contact is made after said manual movement for said predetermined distance, said electrical contact actuating said electrically actuated power cylinder.

11. A power grip structure as recited in claim 1, wherein a plurality of switches are closed sequentially to control the amount of power from said at least one power cylinder.

12. Power grip structure comprising two elongated members positioned in side by side parallel relation for relative longitudinal movement, means at one end of the members for gripping an object on relative axial movement between the members and at least one electrically actuated power cylinder secured between the elongated members for producing relative axial movement between the members on actuation thereof and means connected to the power cylinders for actuation of the power cylinders:
   wherein the electrically actuated power cylinder includes a piston rod and cylinder, gas in the cylinder which is expandable on application of heat thereto, means operable on expansion of the gas within the cylinder for extending the piston rod out of the cylinder and an electrically operated heater within the cylinder in contact with the gas.

13. A power grip structure as recited in claim 12, wherein a rolling seal is disposed between said piston rod and said cylinder.

14. A power grip structure as recited in claim 12 wherein cooling means are utilized to cool said cylinder.

15. A power grip structure as recited in claim 14, wherein said cooling means includes fins formed at the outer periphery of said cylinder.

16. A power grip structure as recited in claim 15, wherein a fan directs air over said fins in a direction away from said elongated members.

17. A power grip structure as recited in claim 12, wherein said elongated members are utilized for a medical purpose.

18. A power assisted surgeon's rongeur comprising a pair of elongated parallel members positioned in sliding contact with each for relative axial movement, means at one end of the elongated members for gripping material therebetween, a first handle part integrally connected to and extending generally perpendicular to one of the elongated members at the other end thereof, a second handle part extending perpendicularly through the one elongated member at the other end thereof, pivot means operable between the first and second handle parts for pivotally mounting the second handle part on the first handle part adjacent one end of the second handle part, a lost motion connection between the second of the elongated members and the second handle part at the other end thereof whereby relative pivotal movement between the first and second handle parts produces relative longitudinal movement between the elongated members, a pair of electrically actuated power cylinders extending parallel to each other and to the elongated members rigidly mounted on the first handle portion and connected to the second elongated member for producing movement of the second elongated member relative to the first elongated member on actuation thereof and electric means for actuating the power cylinders.

19. Structure as set forth in claim 18 wherein the means for electrically actuating the electrically actuated power cylinders includes a limit switch secured to the second handle portion connected to the electrically actuated power cylinders and to a source of electrical energy and means carried on the second handle member for actuating the limit switch manually in response to a predetermined grip pressure on the rongeur.

20. Structure as set forth in claim 18 and further including an electrically powered blower secured to the rongeur to accelerate heat removal from the cylinders to increase the number of possible cylinder cycles in a fixed period of time.

21. A power assisted surgeon's rongeur comprising a pair of elongated parallel members positioned in sliding contact with each for relative axial movement, means at one end of the elongated members for gripping material therebetween, a first handle part integrally connected to and extending perpendicular to one of the elongated members at the other end thereof, a second handle part extending generally perpendicularly through the one elongated member at the other end thereof, pivot means operable between the first and second handle parts for pivotally mounting the second handle part on the first handle part adjacent one end of the second handle part, a lost motion connection between the second of the elongated members and the second handle part at the other end thereof whereby relative pivotal movement between the first and second handle parts produces relative longitudinal movement between the elongated members, a pair of electrically actuated power cylinders extending parallel to each other and to the elongated members rigidly mounted on the first handle portion and connected to the second elongated member for producing movement of the second elongated member relative to the first elongated member on actuation thereof and electric means for actuating the power cylinders in separate groups.

22. Structure as set forth in claim 21 wherein the means for electrically actuating the electrically actuated power cylinders includes a limit switch secured to the second handle portion connected to the electrically actuated power cylinders and to a source of electrical energy to actuate the electrically actuated power cylinders in two individual groups and means carried on the second handle member for actuating the limit switch at two different levels, manually in response to a predetermined grip pressure on the rongeur.

23. A power grip method comprising positioning two parallel elongated members in side by side parallel relation for movement longitudinally relative to each other, providing means on one end of the longitudinally extending members for gripping material on relative longitudinal movement between the elongated members and moving the elongated members relative to each other longitudinally, by first manually producing relative longitudinal movement between the longitudinal members for a predetermined distance and then actuating an electrically actuated power cylinder means secured between the elongated members; and wherein the manual movement for a predetermined distance completes an electric contact which in turn actuates the electrically actuated power cylinder.

24. The method as set forth in claim 23 and further including actuating the power cylinder means in a plurality of steps.

25. The method as set forth in claim 23 wherein the power cylinder means includes a plurality of electrically actuated power cylinders secured between the elongated members and further including the step of separately actuating groups of the plurality of electrically actuated power cylinders.

26. The method as set forth in claim 25 and further including actuating the groups of power cylinders in a plurality of steps.

27. The method as set forth in claim 23, wherein manual input must be continued after actuation of the electrically actuated power cylinder.

28. A power grip method comprising positioning two parallel elongated members in side by side parallel relation for movement longitudinally relative to each other, providing means on one end of the longitudinally extending members for gripping material on relative longitudinal movement between the elongated members and moving the elongated members relative to each other longitudinally in response to actuation of electrically actuated power cylinder means secured between the elongated members;

wherein the electrically actuated power cylinder means comprise cylinder and piston rod structure having a gas actuating medium therebetween expandable on application of heat thereto and an electric heater exposed to the gas and actuating the power cylinder means comprises supplying electrical energy to the electrical heater exposed to the gas.

29. Power grip structure comprising two elongated members positioned in side by side parallel relation for relative longitudinal movement, means at one end of the members for gripping an object on relative axial movement between the members, said members being manually moveable relative to each other for a predetermined distance, at least one electrically actuated power cylinder secured between the elongated members for producing relative axial movement between the members on actuation thereof and means connected to the power cylinders for communicating electric energy for actuation of the power cylinders after movement through said predetermined distance wherein manual input must be continued after the actuation of said electrically actuated power cylinder, or said electrically actuated power cylinder will become deactuated.

30. A power grip method comprising positioning two parallel elongated members in side by side parallel relation for movement longitudinally relative to each other to perform work, providing means on one end of the longitudinally extending members for gripping material on relative longitudinal movement between the elongated members and moving the elongated members relative to each other longitudinally to grip material, by first manually producing relative longitudinal movement between the longitudinal members to grip material and then actuating a switch for an electrically actuated power cylinder means secured between the elongated members to provide a power assist for gripping the material; and actuating the switch means while manual input is occurring.

* * * * *